(12) United States Patent
Ramsay et al.

(10) Patent No.: US 8,882,810 B2
(45) Date of Patent: Nov. 11, 2014

(54) CROSSOVER SPINOUS PROCESS IMPLANT

(75) Inventors: Christopher Ramsay, Raynham, MA (US); Christine Rusbarsky, Raynham, MA (US); Katherine Selover, Raynham, MA (US); Glen Presbrey, Raynham, MA (US); Hassan Serhan, Raynham, MA (US)

(73) Assignee: DePuy Synthes Products, LLC, Raynham, MA (US)

( * ) Notice: Subject to any disclaimer, the term of this patent is extended or adjusted under 35 U.S.C. 154(b) by 38 days.

(21) Appl. No.: 13/559,919

(22) Filed: Jul. 27, 2012

(65) Prior Publication Data

US 2013/0030471 A1    Jan. 31, 2013

Related U.S. Application Data

(63) Continuation-in-part of application No. 12/712,578, filed on Feb. 25, 2010, now Pat. No. 8,246,656.

(51) Int. Cl.
*A61B 17/88* (2006.01)
*A61B 17/70* (2006.01)

(52) U.S. Cl.
CPC .................................. *A61B 17/7065* (2013.01)
USPC ........................................................ 606/279

(58) Field of Classification Search
CPC .................................................... A61B 17/7065
USPC ......... 606/246–253, 257, 276, 279, 105, 198, 606/90; 623/17.11–17.16; 411/75–80
See application file for complete search history.

(56) References Cited

U.S. PATENT DOCUMENTS

| | | | |
|---|---|---|---|
| 4,404,967 A | 9/1983 | Bacal et al. |
| 5,092,889 A | 3/1992 | Campbell, Jr. |
| 5,393,036 A | 2/1995 | Sheridan |
| 5,496,318 A | 3/1996 | Howland |
| 5,609,634 A | 3/1997 | Voydeville |
| 5,741,254 A | 4/1998 | Henry |
| 6,322,500 B1 | 11/2001 | Sikora et al. |
| 6,375,656 B1 | 4/2002 | Faure |
| 6,402,751 B1 | 6/2002 | Hoeck et al. |
| 6,451,019 B1 | 9/2002 | Zucherman |
| 6,451,020 B1 | 9/2002 | Zucherman |
| 6,652,527 B2 | 11/2003 | Zucherman |
| 7,201,751 B2 | 4/2007 | Zucherman |

(Continued)

FOREIGN PATENT DOCUMENTS

| | | |
|---|---|---|
| EP | 1334703 | 8/2003 |
| WO | WO 94/23660 | 10/1994 |

(Continued)

OTHER PUBLICATIONS

Bradney IW: Repair of a fracture/dislocation of lumbar vertebrae in a French poodle. *Aust Vet J* 43:421, 1967.

(Continued)

*Primary Examiner* — Pedro Philogene
(74) *Attorney, Agent, or Firm* — Thomas M. DiMauro

(57) ABSTRACT

A device intended for the treatment of spinal stenosis. This device is an inter-spinous spacer that is introduced through a single posterior incision. It uses a single piece insertion technique with a unilateral approach. The surgeon does not need to access the opposite side of the spinous process. It allows the user infinite adjustability in distraction height with a single locking mechanism.

7 Claims, 3 Drawing Sheets

(56) References Cited

U.S. PATENT DOCUMENTS

Figure 1:
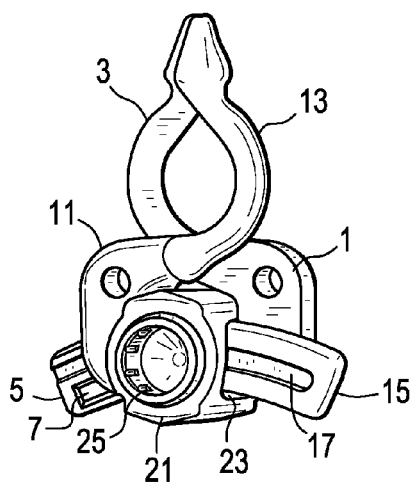

| | | |
|---|---|---|
| 7,530,991 B2 | 5/2009 | Nekozuka |
| 7,588,601 B2 * | 9/2009 | Le Couedic et al. ........ 623/17.16 |
| 7,883,532 B2 * | 2/2011 | Biscup et al. ................. 606/324 |
| 7,993,371 B2 * | 8/2011 | Farris ............................ 606/246 |
| 8,025,678 B2 * | 9/2011 | Reynolds et al. ............. 606/249 |
| 8,048,118 B2 * | 11/2011 | Lim et al. ...................... 606/249 |
| 8,357,181 B2 * | 1/2013 | Lange et al. .................. 606/248 |
| 8,425,561 B2 * | 4/2013 | Lim et al. ...................... 606/249 |
| 2002/0029039 A1 | 3/2002 | Zucherman et al. |
| 2002/0123754 A1 | 9/2002 | Holmes et al. |
| 2005/0240182 A1 | 10/2005 | Zucherman |
| 2007/0162000 A1 | 7/2007 | Perkins |
| 2007/0203495 A1 | 8/2007 | Zucherman |
| 2008/0033445 A1 | 2/2008 | Zucherman |
| 2008/0058806 A1 | 3/2008 | Klyce |
| 2008/0058807 A1 | 3/2008 | Klyce |
| 2008/0058808 A1 | 3/2008 | Klyce |
| 2008/0058941 A1 | 3/2008 | Zucherman |
| 2008/0065086 A1 | 3/2008 | Zucherman |
| 2008/0086212 A1 | 4/2008 | Zucherman |
| 2008/0167655 A1 | 7/2008 | Wang |
| 2008/0167656 A1 | 7/2008 | Zucherman |
| 2008/0177271 A1 | 7/2008 | Yeh |
| 2008/0288075 A1 | 11/2008 | Zucherman |
| 2009/0204148 A1 | 8/2009 | Lenke et al. |
| 2009/0222043 A1 | 9/2009 | Altarac et al. |
| 2009/0248076 A1 | 10/2009 | Reynolds |
| 2009/0248079 A1 | 10/2009 | Kwak |
| 2010/0249840 A1 * | 9/2010 | Tanaka ........................... 606/249 |
| 2011/0144692 A1 * | 6/2011 | Saladin et al. ................ 606/249 |

FOREIGN PATENT DOCUMENTS

| | | |
|---|---|---|
| WO | WO 96/21396 | 7/1996 |
| WO | WO 99/18877 | 4/1999 |
| WO | WO 2007/146928 | 12/2007 |

OTHER PUBLICATIONS

Harmon H, Hugenberg JE: Surgical repair of a vertebra in a dog. *J Am Vet Med Assoc* 149:46, 1966.

Hoerlein BF: Methods of spinal fusion and vertebral immobilization in the dog. *Am J Vet Res* 17:685, 1956.

Hurov, L., Can. Vet. Jour., vol. 4, No. 5, May, 1963, 128-132.

Liu et al. "Endoscopic decompression combined with interspinous process implant fusion for lumbar spinal stenosis", Chin J Traumatol. 2008; 11(6):364-7.

Lumb WY, Brasmer TH: Partial vertebral prosthesis in a dog. J Am Vet Med Assoc 155:1581, 1969.

Neo et al., *J Neurosurg Spine*, 2006 Jan;4(1):78-81.

International Search Report re: PCT/US2011/025649 dated Apr. 19, 2011.

* cited by examiner

CROSSOVER SPINOUS PROCESS IMPLANT

CONTINUING DATA

This application claims priority from co-pending application U.S. Ser. No. 12/712,578, Ramsey et al., filed Feb. 25, 2010, and entitled "Crossover Spinous Process Implant", the specification of which is incorporated by reference in its entirety.

BACKGROUND OF THE INVENTION

The leading cause of lower back pain arises from rupture or degeneration of lumbar intervertebral discs. Pain in the lower extremities can be caused by the compression of spinal nerve roots by a bulging disc, while lower back pain is caused by collapse of the disc and by the adverse effects of articulation weight through a damaged, unstable vertebral joint.

In some cases, when a patient having a collapsed disc moves in extension (e.g., leans backward), the posterior portion of the annulus fibrosis or the ligamentum flavum may further compress and extend into the spinal canal. This condition, called "spinal stenosis", narrows the spinal canal and causes impingement of tissue upon the spinal cord, thereby producing pain.

There have been numerous attempts to provide relief for these afflictions by providing a spacer that inserts between adjacent spinous processes present in the posterior portion of the spinal column. This spacer essentially separates the upper spinous process from the lower spinous process, thereby relieving stenosis. In general, these interspinous implants are adapted to allow flexion movement in the patient, but resist or limit extension.

There are numerous publications disclosing interspinous process spacers having a strut-like body disposed between the spinous processes. See, for example, U.S. Pat. Nos. 6,451,019; 6,451,020; 6,652,527; 7,201,751, US Patent Publication No. 2005-0240182, US Patent Publication No. 2007-0203495, US Patent Publication No. 2008-0033445, US Patent Publication No. 2008-0058941, US Patent Publication No. 2008-006586, US Patent Publication No. 2008-0086212, US Patent Publication No. 2008-0167656, and US Patent Publication No. 2008-0288075.

US Patent Publication No. 20080167655 (Wang) discloses devices, tools and methods for minimally invasive implantation and distraction between spinous processes for treatment of spinous disorders. Wang discloses an interspinous implant device for distracting at least one pair of adjacent spinous processes includes a main body including a shaft having a longitudinal axis; and first and second parallel arms extending transversely from the main body, wherein at least one of the first and second parallel arms is slidably mounted with respect to the shaft. The parallel arms are configured and dimensioned to extend laterally from both sides of the spinous processes when implanted therebetween and to be inserted between the spinous processes laterally from a single side thereof. The parallel arms are variably positionable between a closed configuration, in which the parallel arms are positioned close to or in contact with one another, to facilitate insertion of the parallel arms between the adjacent spinous processes, and an open configuration, in which the parallel arms are separated from one another.

US Patent Publication No. 2007-0162000 (Perkins) discloses an adjustable spacing device configured to be placed between the spinous processes of at least two adjacent vertebrae and a method of using the device to treat spinal stenosis by restricting extension and allowing normal flexion of adjacent vertebrae relative to one another. Perkins discloses an implant having a horizontal member attached to two legs, one on each side of the spinous process.

US Patent Publication No. 2008-0177271 (Yeh) discloses an implant having a center axle for rotation of the two pieces during insertion. Yeh discloses an interspinous process distraction device including a male distraction element and a female distraction element, which both have a clamping portion for fixedly pushing and rejecting the interspinous processes and also respectively have a first connecting portion and a second connecting portion connected at the other end of the clamping portion. Here, the first connecting portion and the second connecting portion are paired for blocking with each other so as to form the interspinous process distraction device capable of having an opposite rotation. Besides, through clamping two interspinous processes which stress the nerve by the male distraction element and the female distraction element and rotating them to oppositely rotate, the two interspinous processes can therefore be moved to be in alignment as the normal condition.

U.S. Pat. No. 5,393,036 (Sheridan) discloses an implant driven with a screw or threads to create distraction.

U.S. Pat. No. 5,496,318 (Howland) discloses an implant having an H-shape or belt to secure the implant. Howland discloses a spinal fixation device and method for the stabilization of the spine after surgical procedures such as those related to degenerative disc diseases. The device comprises a spacer, which is placed between adjacent vertebrae when installed and a locking mechanism attached to the spacer. The locking mechanism attaches the device to the spinous processes of adjacent vertebrae of the spine in a manner which is non-invasive with respect to the vertebrae to which it is attached.

U.S. Pat. No. 5,092,889 (Forte) discloses an implant held in place by wrapping around the ribs to provide stabilization in compression or distraction.

US Patent Publication Nos. 20090248076 (Reynolds) and 20090248079 (Kwak) each discloses an interspinous spacer having a pair of hooks that, upon lateral insertion between opposed spinous process, bear upon the opposed spinous processes.

SUMMARY OF THE INVENTION

The device of the present invention is intended for the treatment of spinal stenosis. This device is an inter-spinous spacer that is introduced through a single posterior incision. It uses a single piece insertion technique with a unilateral approach. The surgeon does not need to access the opposite side of the spinous process. It allows the user infinite adjustability in distraction height with a single locking mechanism.

The implant of the present invention generally has four components:
a) Top body—for contacting the superior spinous process it includes 1) a hook shaped portion with angled contact surface, 2) a curved track with grooves to interface with the grooves on the bottom body, and 3) insertion feature or hole;
b) Bottom body—for contacting the inferior spinous process it includes 1) a hook shaped portion with angled contact surface, 2) a curved track with grooves to interface with the grooves on the top body, and 3) insertion feature or hole;
c) Housing—has a throughbore (or slot) that contains the curved tracks of the top and bottom bodies as well as the set screw. The housing further has a threaded recess that accepts a set screw. The housing further has a mating feature (such as a pin) to help constrain the tracks of the top and bottom bodies; and d) Set screw—threads into the housing threaded recess and compresses the curved track of the top and bottom bodies. The set screw also has a mating feature (such as a pin) to help constrain the tracks of the top and bottom bodies.

The device of the present invention has many advantages:
a) The implant's geometry allows for placement between the spinous processes followed by distraction of the spinous processes. In contrast, other conventional spinous process implants distract the spinous processes while they are being inserted.
b) Each of the body components of the device has an integrated track with grooves to interface with the opposite body. The advantage of the grooves is that it allows for infinite adjustability. It also provides stability to the construct.
c) The curve of the track allows more distraction with a smaller profile.

DESCRPTION OF THE FIGURES

FIG. 1 discloses a top view of the present invention in the collapsed state.

Figure 2:
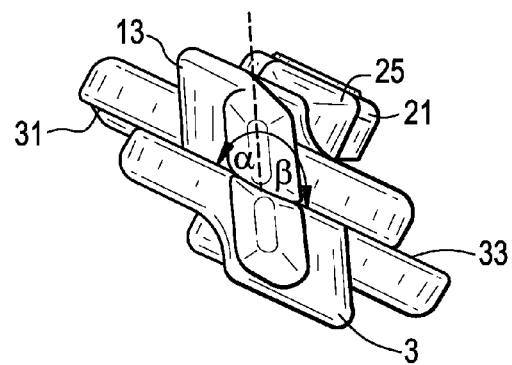

FIG. 2 discloses an insertion profile view of the present invention in the collapsed state.

Figure 3:
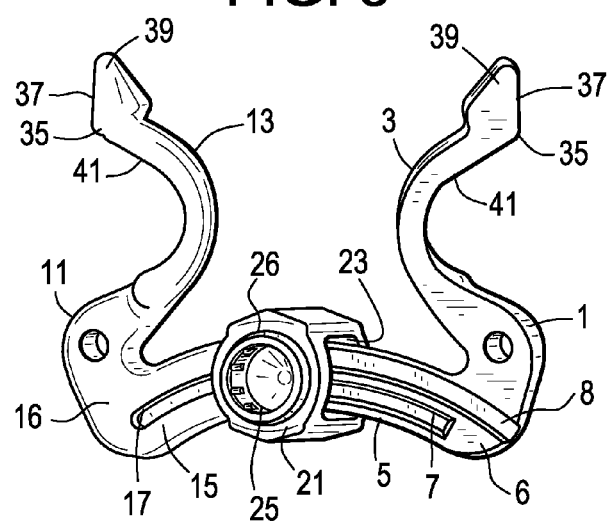

FIG. 3 discloses a top view of the present invention in the expanded state.

Figure 4:
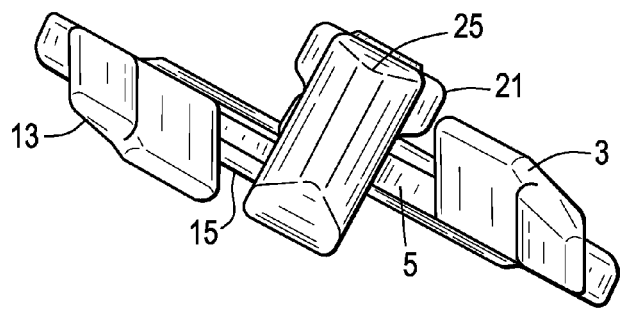

FIG. 4 discloses an insertion profile view of the present invention in the expanded state.

Figure 5:
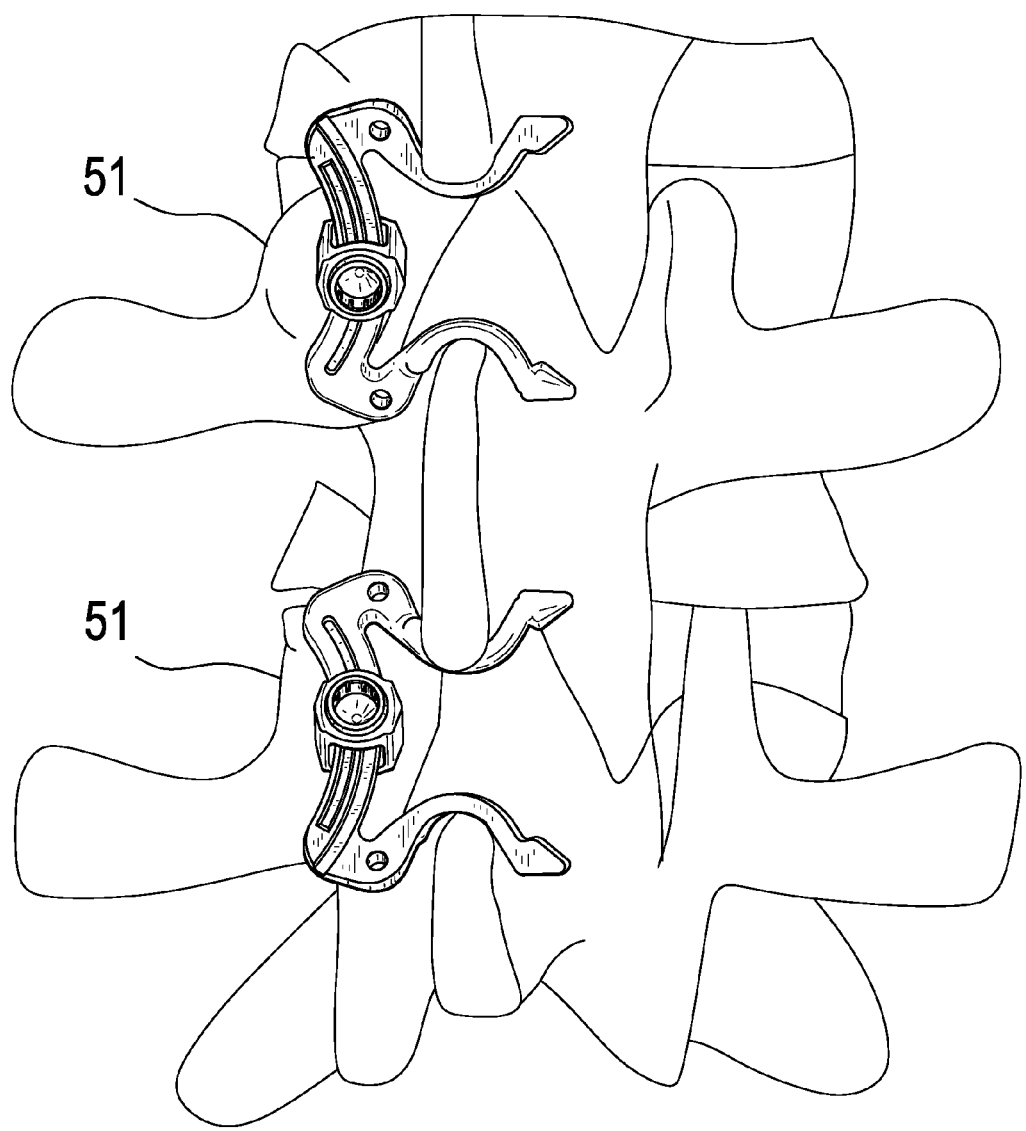

FIG. 5 discloses a pair of devices of the present invention implanted on a spine.

Figure 6A:
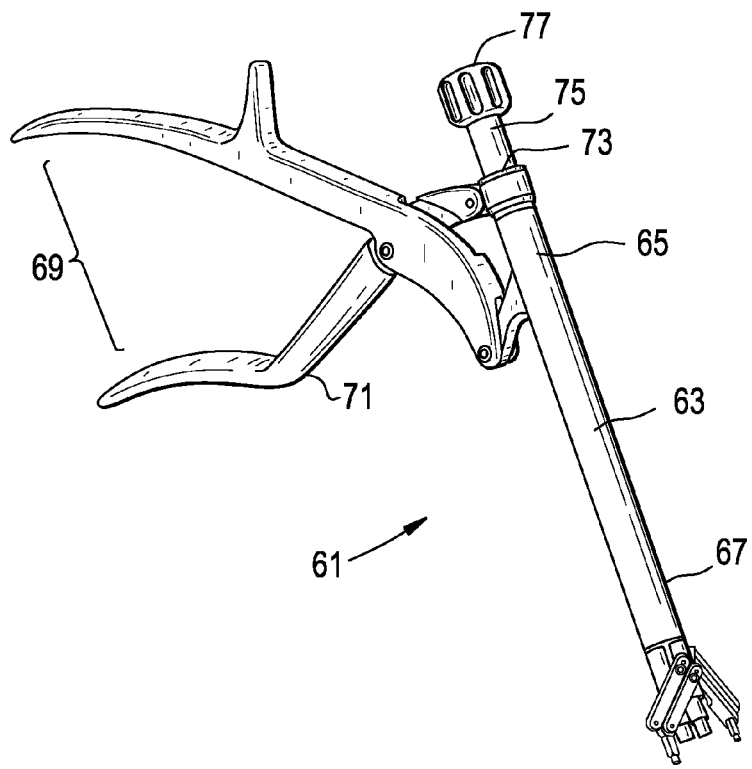
Figure 6B:
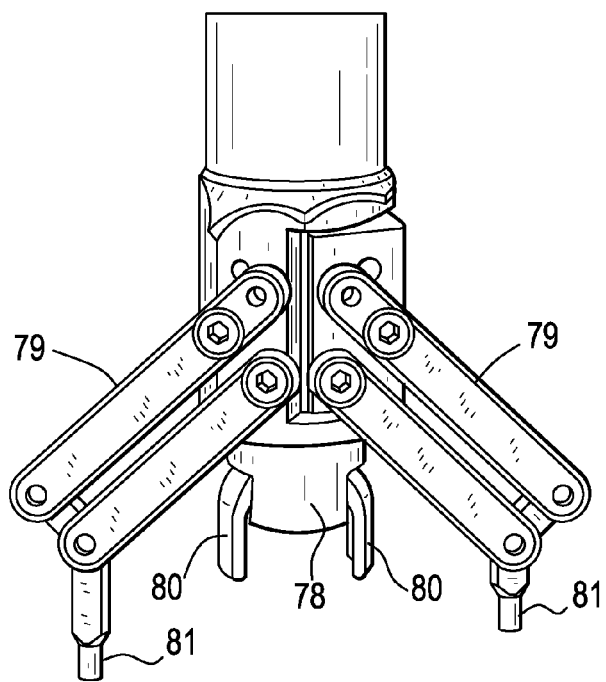

FIGS. 6*a* and 6*b* disclose an inserter of the present invention.

DETAILED DESCRIPTION

Referring now to FIGS. 1-4, there is provided an interspinous process device, comprising:
a) a first body 1, the first body comprising i) a first hook-shaped portion 3 adapted for contacting a superior spinous process, and ii) a first curved track portion 5 having a first face 6 and a second face (not shown), the first face 6 having a groove 8 therein and a rail 7 thereon running parallel to the groove, the second face having a groove therein running parallel to the groove of the first face;
b) a second body 11, the second body comprising i) a second hook-shaped portion 13 adapted for contacting an inferior spinous process, ii) a second curved track portion 15 having a first face 16 and a second face (not shown), the first face 16 having a groove 17 therein, the second face having a groove therein and a rail thereon,
c) a housing 21 having i) a slot 23 therethrough slidably receiving the curved track portions, ii) a threaded throughhole 26 extending in a direction transverse to the slot, and a containing pin (not shown) extending into the slot
d) a set screw 25 adapted for compressing the curved track portions of the first and second bodies, the set screw having i) a peripheral thread threadably received in the throughhole of the housing, and ii) an end face (not shown) having a constraining feature (such as a pin) adapted to constrain the curved track portions,
wherein the rail and groove of the second face of the second body respectively slidingly engage the groove and rail of the first face of the first body,
wherein the groove of the first face of the second body slidingly engages the constraining feature of the set screw, and
wherein the groove of the second face of the first body slidingly engages the containing pin of the housing.

In some embodiments, each hook has an acutely angled face to more closely match the angle of the posterior-most portion of the spinous process it contacts. In contrast, the hooks of some conventional spinous process implants have a face that is perpendicular to the distraction path. In the present invention, a first mating face 31 forms an acute angle α which is less than 90 degrees with respect to the tips, while the second mating face 33 forms an obtuse angle β which is more than 90 degrees with respect to the tips.

Therefore, in accordance with the present invention, there is provided an interspinous process device, comprising:
a) a first hook-shaped portion adapted for contacting a first spinous process,
b) a second hook-shaped portion adapted for contacting a second spinous process,
c) a connector portion adapted to adjustably connect the first and second hook-shaped portions,
wherein the first hook-shaped portions has acutely angled contact surface, and wherein the second hook-shaped portion has an obtusely angled contact surface.

In some embodiments, each track has an arc shape, which allows for increasing the hook depth as distraction increases. Therefore, in accordance with the present invention, there is provided an interspinous process device, comprising:
a) a first hook-shaped portion adapted for contacting a superior spinous process,
b) a second hook-shaped portion adapted for contacting an inferior spinous process,
c) an arced connector portion adapted to adjustably connect the first and second hook-shaped portions.

In one arced embodiment, the arc forms a convex surface facing the hooked-shaped portions. In a second arced embodiment, the arc forms a concave surface facing the hooked-shaped portions. In preferred embodiments, the arc defines a radius of between about 2 cm and about 5 cm.

In preferred embodiments, the implant has a single locking mechanism. The requirement of only a single locking mechanism minimizes the amount of time the surgeon must spend stabilizing the device. Therefore, in accordance with the present invention, there is provided an interspinous process device, comprising:
a) a first hook-shaped portion adapted for contacting a superior spinous process,
b) a second hook-shaped portion adapted for contacting an inferior spinous process,
c) a adjustable connector portion adapted to adjustably connect the first and second hook-shaped portions,
d) a single lock (such as a set screw) adapted to lock the adjustable connector portion.

In some embodiments, the set screw tightens upon an outer end portion of each track to produce an expanded hook state. In some embodiments, the inner end portion of each track is received in the housing to produce a collapsed hook state.

In some embodiments, each hook-shaped portion has an inflection point 35 in each outer end portion. The inflection point allows the concave side 37 of the hook tip 39 (i.e., the side of the tip associated with the concave face 41 of the hook) to contact the spinous process during insertion. The geometry of these hooks allows their insertion between the spinous processes without distracting the spinous processes. The hooks' subsequent distraction (upon actuation of the inserter) produces similar distraction in the spinous processes. In contrast, in other conventional interspinous process spacers (which do not contain an inflection point), the convex portion of the hook tip (i.e., the side of the tip associated with the convex portion of the hook) distracts the spinous processes as the implant is being inserted. Therefore, the inflection point provides an advantage in that both hooks are passed between the spinous processes at the same time, thus insuring full capture of the spinous processes before distraction. Therefore, in accordance with the present invention, there is provided an interspinous process device, comprising:
  a) a first hook-shaped portion adapted for contacting a superior spinous process,
  b) a second hook-shaped portion adapted for contacting an inferior spinous process,
  c) a connector portion adapted to adjustably connect the first and second hook-shaped portions,
wherein the first and second hook-shaped portions each have an inflection point.

In addition, the tips are bulleted to more easily puncture the ligament.

In some embodiments, at least one track has a longitudinal groove 7,17 therein, and the tracks are oriented in the housing so that the longitudinal grooves nest. Thus, each body component has an integrated track with grooves to interface with the opposite body. Therefore, in accordance with the present invention, there is provided an interspinous process device, comprising:
  a) a first hook-shaped portion adapted for contacting a superior spinous process,
  b) a second hook-shaped portion adapted for contacting an inferior spinous process,
  c) a connector portion adapted to adjustably connect the first and second hook-shaped portions,
wherein the connector portion comprises first and second track portions having mating grooves.

In some embodiments, the first and second bodies are oriented so that the hook-shaped portions open in opposite directions in the expanded state.

In some embodiments, the housing has a mating feature to constrain the tracks in the housing. In particular, this mating feature is a pin that prevents groove 17 from sliding all the way out of the housing, thereby preventing disassembly.

In some embodiments, the set screw has a mating feature to constrain the tracks in the housing. In particular, this mating feature is a pin that prevents groove 17 from sliding all the way out of the housing, thereby preventing disassembly.

In some embodiments, the threaded recess extends into the housing in a third direction, and the throughbore extends through the housing in a fourth direction substantially perpendicular to the third direction of the threaded recess.

In some embodiments, each body further comprises iii) an intermediate portion connecting the inner end portion of the first hook-shaped portion to the inner end portion of the first longitudinal track.

With correct material selection, the implant can be rigid for fusion, or have a spring-like action for non-fusion applications.

Therefore, in some embodiments, there is provided a method of using an interspinous spacer having a collapsed condition and an expanded condition, the method comprising the steps of:
  a) inserting the spacer in its collapsed condition into an interspinous space of a patient that has been selected for spinal fusion,
  b) expanding the spacer.

In some embodiments, the site at which the spinal fusion is desired is the intervertebral disc space. Preferably, some graft material and an intervertebral fusion cage is inserted into the disc space, preferably by a lateral approach. Therefore, the patient receives both the spacer of the present invention within an interspinous space (preferably with graft) and an intervertebral fusion cage (also preferably with graft) in the disc space).

In some embodiments, the fusion site is an interspinous process site. Spinal process fixation on the easily accessible dorsal processes of the spine represents one of the earliest historically acceptable means to accomplish segmental stability in the spine. See Bradney I W: Repair of a fracture/dislocation of lumbar vertebrae in a French poodle. *Aust Vet J* 43:421, 1967; Harmon H, Hugenberg J E: Surgical repair of a vertebra in a dog. *J Am Vet Med Assoc* 149:46, 1966; Hoerlein B F: Methods of spinal fusion and vertebral immobilization in the dog. *Am J Vet Res* 17:685, 1956; Hurov L: Spinal fracture plating. *SAC* 58:441, 1962; and Lumb W Y, Brasmer T H: Partial vertebral prosthesis in a dog. *J Am Vet Med Assoc* 155:1581, 1969. Posterior interspinous decompression in conjunction of spinous process fixation offers significant immediate stability as it provide resistance to flexion and rotation, however, this stability is limited by the relative strength of the spinous processes and implant stiffness. See Neo M, Fujibayashi S, Yoshida M, Nakamura T, Spinous process plate fixation as a salvage operation for failed anterior cervical fusion, technical note, *J Neurosurg Spine*, 2006 January; 4(1):78-81; Liu G, Zhao J N, Dezawa A. "Endoscopic decompression combined with interspinous process implant fusion for lumbar spinal stenosis", *Chin J Traumatol*. 2008 December; 11(6):364-7.

In one embodiment, a procedure producing posterior interspinous decompression in conjunction of spinous process fixation may be carried out as follows:

After surgical exposure of the interspinous process space, the surgical technique begins with removal of the interspinous ligaments and contouring the bone edges of the adjacent segment inferior and superior aspects of the spinous processes. A small amount of distraction is applied, and next the lamina is thinned out with a burr. Then, a curette is used to identify the ligamentum flavum. A small rongeurs is used to remove the bone covering the nerves. Then, a curette is used to lift the ligaments from the nerve and decompress the dura. A small rongeurs is then used to cut the ligaments and complete the decompression until the dura is seen as shining. Then, bone graft can be placed between the spinous processes, and the spacer is finally placed and locked after compressing the graft. The graft is held in place by the compression force applied by the spinous process fixation device. This virtually ensures subsequent bone fusion and offers substantial acute stability. This technique significantly diminishes translational mobility at the unstable segment. It also minimizes hyperextension at the unstable segment via medial compression of the grafts into the interspinous space. The fusion of a minimal number of spinal segments should be emphasized. This substantially diminishes the chance of flexible kyphosis and degenerative changes, both above and below the fusion site.

In some embodiments, the site at which the spinal fusion is desired is an interspinous process space. Preferably, some graft material and the spacer are inserted into the interspinous space. Therefore, the patient receives both the spacer of the present invention within an interspinous space (preferably with graft).

FIG. 5 discloses a pair of devices 51 of the present invention implanted on a spine. The angled faces of the devices put the devices in an orientation that allows multiple implants to be implanted without contacting each other.

FIGS. 6a and 6b disclose an inserter 61 of the present invention. In particular, the inserter comprises:
- a) a longitudinal barrel 63 having a proximal end portion 65 and a distal end portion 67,
- b) a pistol grip 69 formed on the proximal end portion of the barrel, the pistol grip having a lever 71, and
- c) a shaft 73 disposed in the barrel and having a proximal end portion 75 and a distal end portion 78 having a pair of teeth 80 extending therefrom,
- d) a knob 77 formed on the proximal end portion of the knob, and
- e) a pair of linkages 79 formed on the distal end portion 78 of the shaft, each linkage having a distal pin 81.

Actuation of the lever on the inserter serves to distract the implant.

Actuation of the knob on the inserter serves to actuate the teeth to hold the housing.

In use, the pin components of the inserter fits into the insertion features (holes) present on each of the bodies of the implant of the present invention. During insertion, the inserter is actuated so that the linkages are in an essentially parallel state and the pins are relatively close together to reflect the collapsed state of the implant. During distraction, the inserter is actuated so that the linkages are in an essentially perpendicular state (as shown in FIGS. 6a and 6b) and the pins are relatively far apart to reflect the expanded state of the implant.

The components of the device of the present invention could be metal, plastic, or ceramic.

If a metal is chosen as the material of construction for a component, then the metal is preferably selected from the group consisting of nitinol, titanium, titanium alloys (such as Ti-6Al-4V), chrome alloys (such as CrCo or Cr—Co—Mo) and stainless steel.

If a polymer is chosen as a material of construction for a component, then the polymer is preferably selected from the group consisting of polycarbonates, polyesters, (particularly aromatic esters such as polyalkylene terephthalates, polyamides; polyalkenes; poly(vinyl fluoride); PTFE; polyarylethyl ketone PAEK; and mixtures thereof.

In some embodiments, the components could be made of a stainless steel alloy, preferably BioDur™ CCM Plus™ Alloy available from Carpenter Specialty Alloys, Carpenter Technology Corporation of Wyomissing, Pa. In some embodiments, the component is made from a composite comprising carbon fiber. Composites comprising carbon fiber are advantageous in that they typically have a strength and stiffness that is superior to neat polymer materials such as a polyarylethyl ketone PAEK. In some embodiments, the component is made from a polymer composite such as a PEKK-carbon fiber composite.

In some embodiments, the composite comprising carbon fiber further comprises a polymer. In some embodiments, the polymer is a polyarylethyl ketone (PAEK). In some embodiments, the PAEK is selected from the group consisting of polyetherether ketone (PEEK), polyether ketone ketone (PEKK) and polyether ketone (PEK). In some embodiments, the PAEK is PEEK.

In some embodiments, the carbon fiber comprises between 1 vol % and 60 vol % (more preferably, between 10 vol % and 50 vol %) of the composite. In some embodiments, the polymer and carbon fibers are homogeneously mixed. In others, the material is a laminate. In some embodiments, the carbon fiber is present in a chopped state. In some embodiments, the chopped carbon fibers have a median length of between 1 mm and 12 mm, such as between 4.5 mm and 7.5 mm. In some embodiments, the carbon fiber is present as continuous strands.

In some embodiments, the composite comprises:
- a) 40-99% (more preferably, 60-80 vol %) polyarylethyl ketone (PAEK), and
- b) 1-60% (more preferably, 20-40 vol %) carbon fiber, wherein the polyarylethyl ketone (PAEK) is selected from the group consisting of polyetherether ketone (PEEK), polyether ketone ketone (PEKK) and polyether ketone (PEK).

In some embodiments, the composite consists essentially of PAEK and carbon fiber. In some embodiments, the composite comprises 60-80 wt % PAEK and 20-40 wt % carbon fiber. For example, the composite may comprise 65-75 wt % PAEK and 25-35 wt % carbon fiber.

We claim:

1. A method of using an interspinous spacer having a collapsed condition and an expanded condition, the method comprising the steps of:
   a) inserting the interspinous spacer in its collapsed condition into an interspinous space of a patient that has been selected for spinal fusion,
   b) expanding the interspinous spacer, and
   c) fusing at least a portion of the spine of the patient,
   wherein the interspinous spacer comprises:
      a) a first body, the first body comprising i) a first hook-shaped portion adapted for contacting a superior spinous process, and ii) a first track portion having a first groove therein,
      b) a second body, the second body comprising i) a second hook-shaped portion adapted for contacting an inferior spinous process, ii) a track portion having a groove therein,
      c) a housing having i) a slot therethrough slidably receiving the track portions, ii) a threaded throughhole extending in a direction transverse to the slot,
      d) a set screw adapted for compressing the track portions of the first and second bodies, the set screw having i) a peripheral thread threadably received in the throughhole of the housing,
   wherein the first and second bodies are slidingly received in the housing, and
   wherein the first body slidingly engages the second body.

2. The method of claim 1 wherein the spinal fusion is carried out at an intervertebral disc space.

3. The method of claim 1 wherein the spinal fusion is carried out at the interspinous space.

4. The method of claim 1 wherein the method achieves posterior interspinous decompression and spinous process fixation.

5. The method of claim 1 further comprising the step of c) manipulating at least one ligament to provide nerve decompression.

6. The method of claim 5 wherein the manipulation comprises lifting the at least one ligament.

7. The method of claim 5 wherein the manipulation comprises cutting the at least one ligament.

* * * * *